United States Patent [19]

Van der Knaap

[11] Patent Number: Plant 6,299

[45] Date of Patent: Sep. 20, 1988

[54] CHRYSANTHEMUM PLANT NAMED HOOF LANE

[75] Inventor: Jacques C. M. Van der Knaap, De Lier, Netherlands

[73] Assignee: Fides Beheer B.V., De Lier, Netherlands

[21] Appl. No.: 915,103

[22] Filed: Oct. 3, 1986

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Schwartz, Jeffery, Schwaab, Mack, Blumenthal & Evans

[57] ABSTRACT

A Chrysanthemum plant named Hoof Lane particularly characterized by its yellow ray floret color and orange disc florets having a surrounding yellow band; nine week response; anemone capitulum; and, by its excellent flower production.

1 Drawing Sheet

1

The present invention comprises a new and distinct cultivar of Chrysanthemum, botanically known as *Chrysanthemum morifolium*, Ramat., and referred to by the cultivar name Hoof Lane.

Hoof Lane was discovered by applicant in 1984 as a spontaneous mutation of Penny Lane, a cultivar of applicant disclosed in a pending application.

Hoof Lane was the result of an induced radiation program conducted by applicant in De Lier, The Netherlands, in 1984. Plants of the parent cultivar Penny Lane were subjected to radiation levels of 1750 rad X-rays. Hoof Lane was discovered and selected as a mutation primarily by virtue of its medium yellow ray floret color, as opposed to the pink ray floret color of Penny Lane.

The first act of asexual reproduction of Hoof Lane was accomplished when vegetative cuttings were taken from the initial selection in August 1984 in a controlled environment in De Lier, The Netherlands by a technician working under formulations established and supervised by Jacques C. M. Van der Knaap. Horticultural examination of selected units initiated in 1984 has demonstrated that the combination of characteristics as herein disclosed for Hoof Lane are firmly fixed and are retained through successive generations of asexual reproduction.

Hoof Lane has not been observed under all possible environmental conditions. The phenotype may vary significantly with variations in environment such as temperature, light intensity and day length. The following observations, measurements and comparisons describe plants grown in De Lier, The Netherlands under greenhouse conditions which approximate those generally used in commercial greenhouse practice.

The following traits have been repeatedly observed and are determined to be basic characteristics of Hoof Lane which, in combination, distinguish this Chrysanthemum as a new and distinct cultivar:

1. Anemone capitulum.
2. Yellow ray floret color, with the color of the disc florets being a medium orange surrounded by a band of yellow.
3. Nine week response.
4. Excellent flower production per stem.
5. Ligulate ray floret form.

Of the many commercial cultivars known to the present inventor, the most similar in comparison to Hoof Lane is the parent cultivar Penny Lane. Hoof Lane is

2 similar to its parent in all essential respects except ray floret color and shape.

The accompanying photographic drawing shows typical inflorescence and foliage characteristics of Hoof Lane, with the color values being depicted as true as possible with photographs of this type.

In the following description, color references are made to The Royal Horticultural Society Colour Chart. The color values were determined between 11:00 a.m. and 12:00 noon in August 1986 under natural daylight at De Lier, The Netherlands.

Classification:

*Botanical.*—*Chrysanthemum morifolium*, Ramat., cv. Hoof Lane.

*Commercial.*—Anemone spray.

INFLORESCENCE

A. Capitulum:
- *Form.*—Flat.
- *Type.*—Anemone.
- *Diameter across face.*—30–55 mm.

B. Corolla of ray florets:
- *Color (general tonality from a distance of three meters).*—Yellow.
- *Color (upper surface).*—8B.
- *Color (under surface).*—4C.

C. Corolla of disc florets:
- *Color (mature).*—Orange-red 34B, with yellow band 12A around the entire periphery.

D. Reproductive organs:
- *Androecium.*—Present in disc florets.
- *Gynoecium.*—Present in both ray and disc florets.

PLANT

A. General appearance:
- *Height.*—75 cm.

B. Foliage:
- *Color (upper surface).*—147A.
- *Color (under surface).*—147B.
- *Shape.*—Lobed and serrated.

I claim:

1. A new and distinct Chrysanthemum plant named Hoof Lane, as described and illustrated, and particularly characterized by its yellow ray floret color and orange disc florets having a surrounding yellow band; nine week response; anemone capitulum; and, excellent flower production.

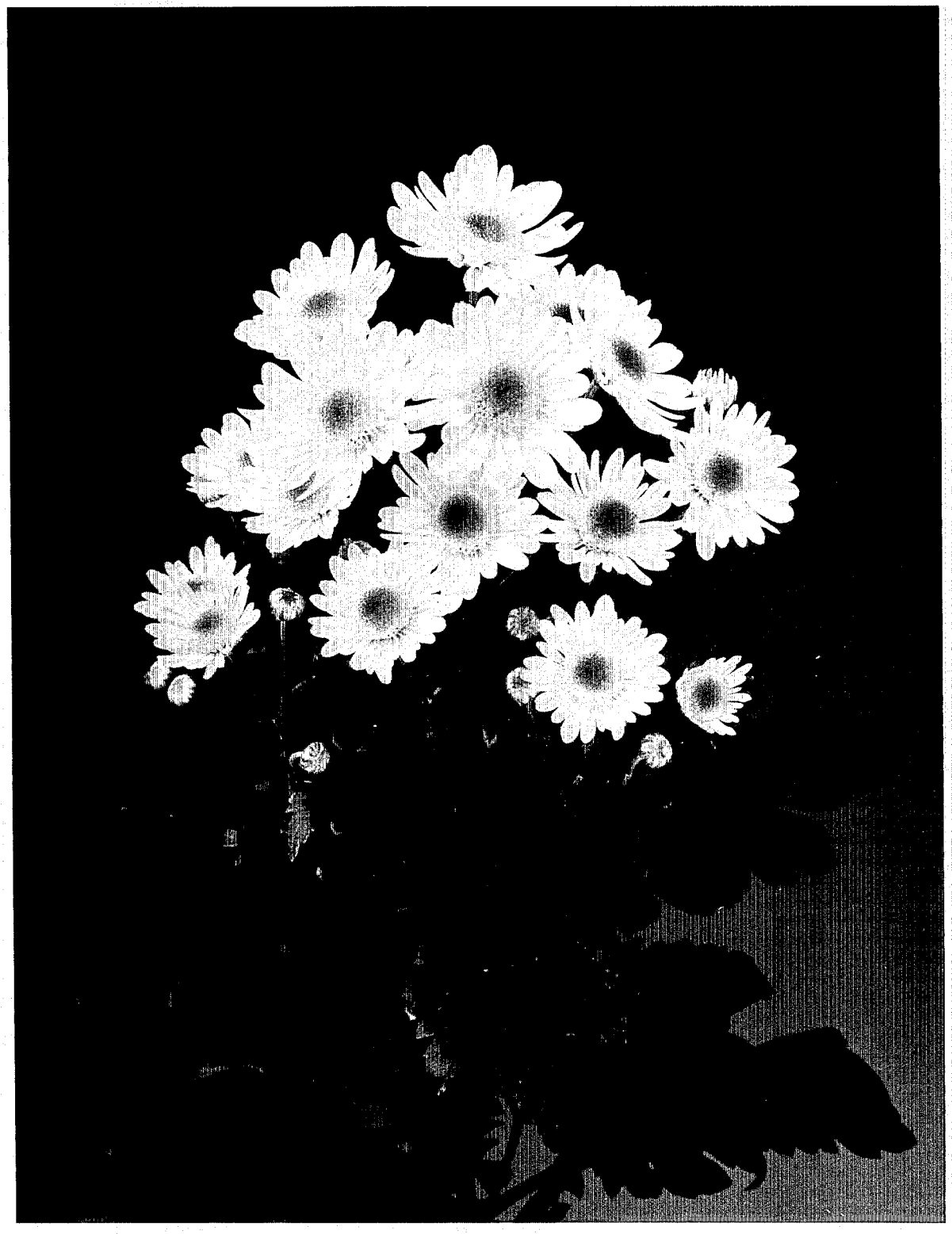

* * * * *